United States Patent [19]
Mienie et al.

[11] Patent Number: 5,559,036
[45] Date of Patent: Sep. 24, 1996

[54] FLUID ANALYSIS

[75] Inventors: Lodewyk J. Mienie, Potchefstroom; Ronald A. Van Steenderen, Pretoria; Elardus Erasmus, Fochville; Julius H. Ueckermann, Pretoria; Wouter J. De Wet; Henning J. Els, both of Potchefstroom, all of South Africa

[73] Assignees: CSIR, Pretoria; Potchefstroom University for Christian Higher Education; Lekratek Instrumentation, both of Potchefstroom, all of South Africa

[21] Appl. No.: 349,264

[22] Filed: Dec. 5, 1994

Related U.S. Application Data

[63] Continuation of Ser. No. 94,489, Jul. 19, 1993, abandoned.

[30] Foreign Application Priority Data

Jul. 20, 1992 [ZA] South Africa .......................... 92/5393

[51] Int. Cl.⁶ .................................................. G01N 33/48
[52] U.S. Cl. .......................... 436/63; 436/145; 422/80; 422/83
[58] Field of Search ........................ 436/63, 145; 422/80, 422/83

[56] References Cited

U.S. PATENT DOCUMENTS

| | | | |
|---|---|---|---|
| 3,958,941 | 5/1976 | Regan | 23/253 |
| 4,277,438 | 7/1981 | Ejzak | 422/80 |
| 4,344,918 | 8/1982 | Takahashi | 422/80 |
| 4,927,767 | 5/1990 | Sakai et al. | 436/64 |

FOREIGN PATENT DOCUMENTS

| | | |
|---|---|---|
| 0256684 | 2/1988 | European Pat. Off. . |
| 3838718 | 6/1989 | Germany . |
| 242371 | 4/1986 | Japan . |

OTHER PUBLICATIONS

"Suggested in Vivo . . . Sites of Administration", Gold et al J. Clin Endocrinol Metals 34:1025, 1972.
Sigma Diagnostics, Procedure No. 555 1988.
European Search Report, Application No. EP 93 30 5647, Berlin, 31 Jan. 1995, corresponding to European counterpart of present application.

*Primary Examiner*—Nina Bhat
*Attorney, Agent, or Firm*—Marshall, O'Toole, Gerstein, Murray & Borun

[57] ABSTRACT

A method and apparatus for the preliminary detection of abnormal levels of metabolites in the urine of a human or mammal. The method includes the steps of determining the amount of creatinine in the urine of the human or animal, measuring the total metabolites content in the urine, using the amount of creatinine in the urine as an internal standard to compensate for variations in the urine concentration, and comparing the total metabolites content in the urine with a reference value which corresponds to the expected total metabolites content in the urine of a person or animal who does not suffer from a metabolic disorder. The apparatus (10) includes an ultraviolet oxidation unit (16) for oxidising total metabolites in a urine sample to carbon dioxide, an organic carbon stripper (18) for stripping carbon dioxide gas from the oxidised sample, and a carbon dioxide detector (69) for measuring the amount of carbon dioxide produced from the sample.

7 Claims, 11 Drawing Sheets

| ORGANIC ACIDURIAS | DETECTION | |
|---|---|---|
| Biotinidase deficiency | 3 3 | 100 |
| Electron transport deficiency | 2 2 | 100 |
| Glutaric aciduria type I | 4 4 | 100 |
| Glutaric aciduria type II | 2 2 | 100 |
| D-Glyceric aciduria | 6 6 | 100 |
| 3-HMG-Co-A lyase deficiency | 2 2 | 100 |
| 4-Hydroxybutyric aciduria | 3 3 | 100 |
| L-2-OH-Glutaric aciduria | 2 2 | 100 |
| Hyperoxaluria | 1 1 | 100 |
| Holocarboxylase synthetase | 2 2 | 100 |
| Isovaleric acidemia | 3 4 | 75 |
| 3-Ketothiolase deficiency | 7 7 | 100 |
| LCAD deficiency | 3 3 | 100 |
| LCHAD deficiency | 2 2 | 100 |
| MCAD deficiency | 5 5 | 100 |
| MSUD | 4 4 | 100 |
| Methylmalonic acidemia | 8 9 | 89 |
| Mevalonic aciduria | 2 2 | 100 |
| 3-MG aciduria type I | 5 5 | 100 |
| 3-MG aciduria type IV | 5 5 | 100 |
| 3-CH3-crotonyl-CoA carboxylase | 2 2 | 100 |
| Pyruvate carboxylase deficiency | 4 4 | 100 |
| Propionic aciduria | 16 18 | 89 |

FLUID ANALYSIS

This is a continuation of U.S. application Ser. No. 08/094,489, filed Jul. 19, 1993, now abandoned.

This invention relates to fluid analysis. More particularly, it relates to a method and apparatus for the preliminary detection of a metabolic disorder in humans as well as animals.

According to the invention there is provided a method for the preliminary detection of abnormal levels of metabolites in the urine of a human or animal suspected of suffering from a metabolic disorder, the method comprising the steps of determining the amount of creatinine in mmol/l in the urine of the human or animal;

measuring the concentration of total urinary metabolites content in the urine, using the amount of creatinine in the urine as an internal standard to compensate for variations in the urine concentration; and comparing the concentration of total urinary metabolites content in the urine with a reference value which corresponds to the expected concentration of total urinary metabolites content in the urine of a human or animal who does not suffer from a metabolic disorder.

Typically, the metabolic disorder includes inborn metabolic disorders including amino acidurias, glycosurias, hyperpurine-pyrimidine urias and organic acidurias.

Said measuring of the concentration of total urinary metabolites content in the urine may be effected in a selected measuring concentration range, typically in the range 50–1000 mmol metabolites/l, eg 50, 100, 200, 400, 600 or 1000 mmol metabolites/l. A urine sample may be diluted with deionised distilled water to adjust the concentration of metabolites to the required concentration range.

The concentration of metabolites in the urine may be measured indirectly by oxidizing the metabolites in the urine to carbon dioxide ($CO_2$), preferably by means of ultraviolet irradiation or by catalytic high combustion, and measuring the amount of $CO_2$ produced. The ultraviolet irradiation is typically enhanced in the presence of an oxidising agent. The amount of $CO_2$ produced is measured, for example, by means of infrared spectroscopy. It may, instead, be measured by means of coulometry, conductivity, gravimetry or colorimetry. The concentration of total urinary metabolites may then be plotted and integrated as a single peak on an electronic integrator using a dedicated computer and program, or using a "SPECTRA PHYSICS" desk integrator or other available desk top integrations.

The concentration of total urinary metabolites may be expressed as a "transformed ratio" (TR) where this ratio lies generally between −1 and +1. The value of the transformed ratio (TR) is calculated as follows:

$$TR = A - B$$

where A=log TUMC

Figure 2:
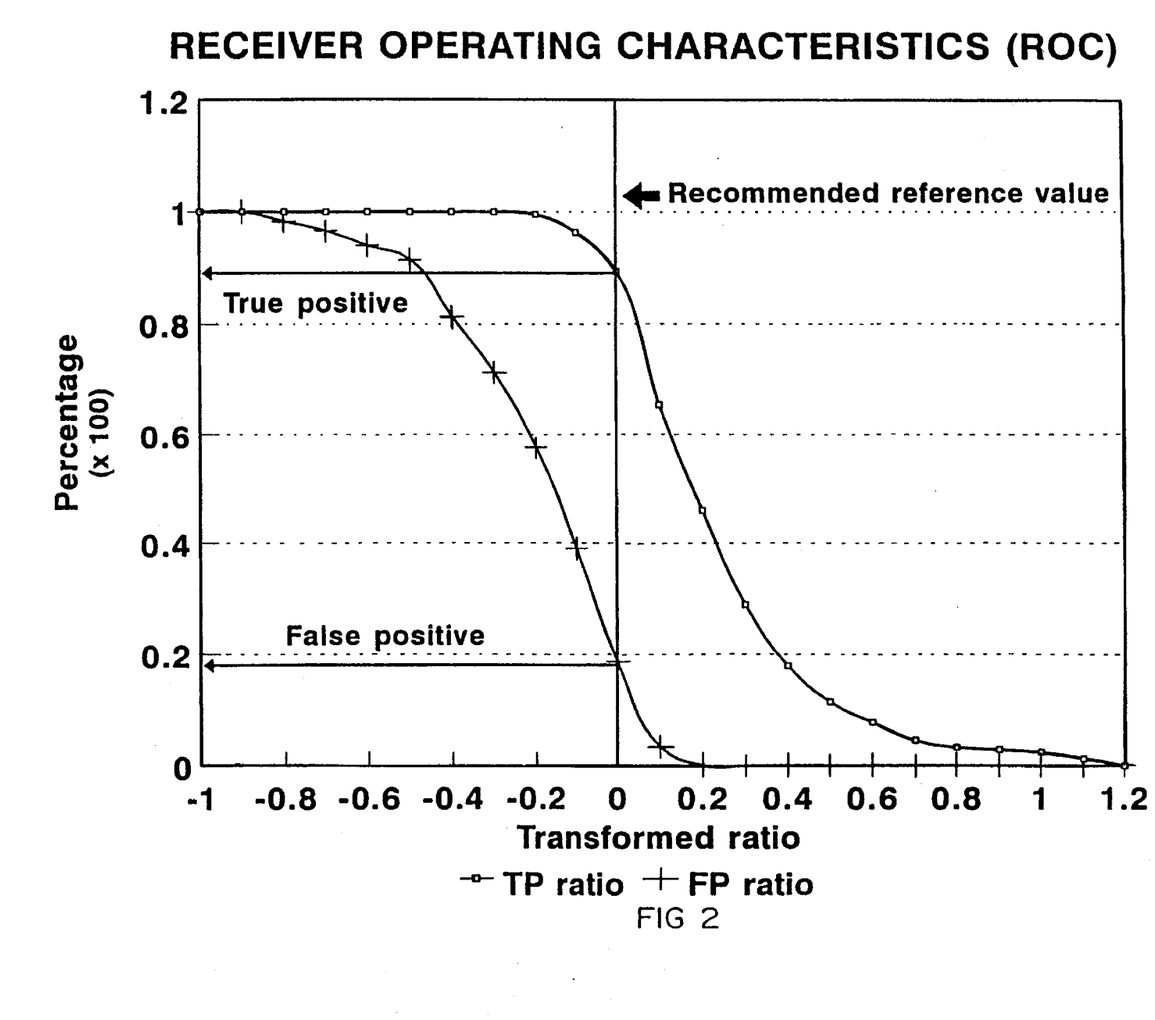
FIG. 2 is a "receiver operating characteristics" (ROC) curve, showing the relation of the true positive (TP) to the false positive (FP) rate and is of special importance in selecting the best reference value (RV)

B=log (urinary creatinine content+1)×C+D where C is a constant, typically 0.906 and D is a constant, typically 1.96 and TUMC represents the total urinary metabolites content in mmol/l. The total urinary metabolites content (TUMC) is the total urinary organic content (TUOC). Said reference value (RV) may be chosen according to the operator's choice. If a reference value (RV) of zero is chosen, then any sample displaying a TR value between 0 and +1 is considered abnormal and any sample displaying a TR value between 0 and −1 is considered normal. Referring to the "receiver operating characteristics" (ROC) plot depicted in FIG. 2 and discussed in further detail below, this would imply a false positive (FP) percentage of 18% and a false negative (FN) percentage of 13%. The sensitivity (SENS) of the test with a reference value (RV) of zero is 90%. This is calculated as follows:

$$SENS = (TP/TP + FN) \times 100$$
= % of disease cases that give a positive result with the RV selected.

The specificity (SPEC) of the test with a reference value (RV) of zero is 82%. This is calculated as follows:

$$SPEC = (TN/TN + FP) \times 100$$
= % of non-disease cases which give a negative result with the RV value selected.

where
TP=True Positives
FP=False Positives
TN=True Negatives
FN=False Negatives

Figure 3:
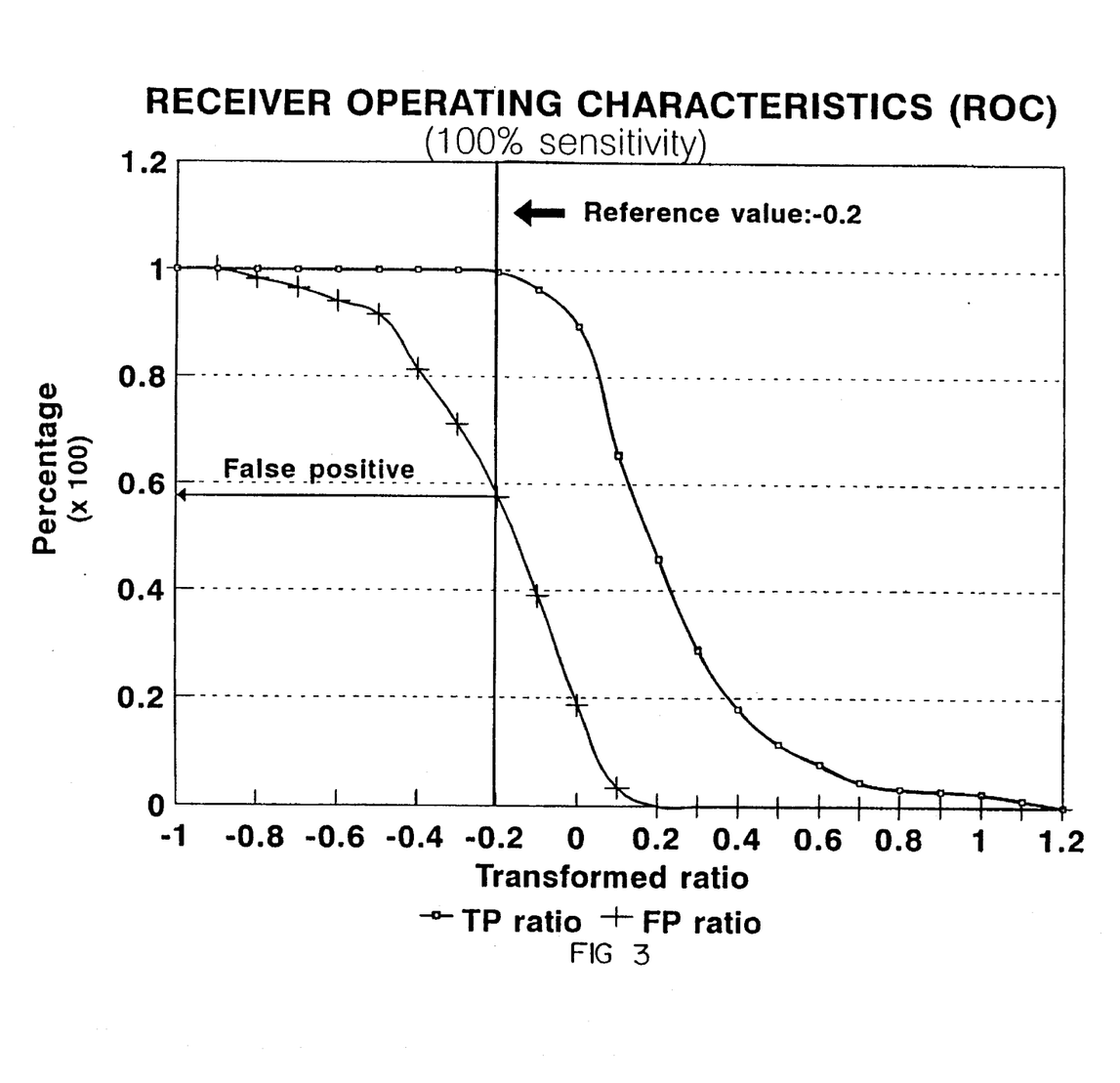
FIGS. 3 and 4 are ROC-plots for 100% sensitivity (SENS) and 100% specificity (SPEC) respectively.
Figure 4:
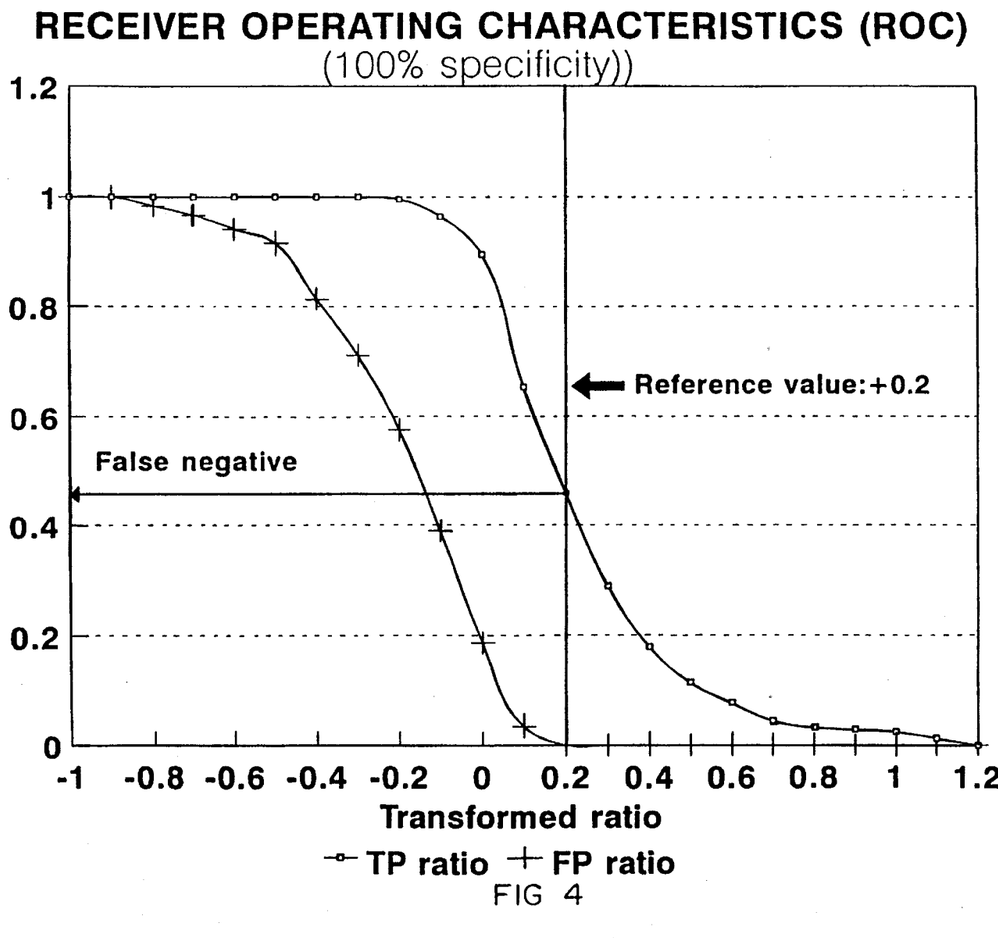

To obtain 100% sensitivity the reference value (RV) may be adjusted to −0.2 on the transformed ratio (TR) scale as depicted in FIG. 3 and discussed in further detail below. This would lead to 58% false positives. To obtain 100% specificity the reference value (RV) may be adjusted to +0.2 on the transformed ratio (TR) scale as depicted in FIG. 4 and discussed in further detail below. This would lead to 46% false negatives.

The method may include the step of removing inorganic material from the urine, prior to measuring the concentration of total urinary metabolites content in the urine.

The invention also extends to apparatus for the preliminary detection of abnormal levels of metabolites in the urine of a human or animal suspected of suffering from a metabolic disorder by the method described above, the apparatus comprising an ultraviolet oxidation unit for oxidising total metabolites in a urine sample to carbon dioxide, the unit comprising an elongate ultraviolet source surrounded by a coil of quartz tubing, the ultraviolet source having a wavelength of 230–260 nm and a power output of 5–1600 watts, the coil having an uncoiled length of 2–16 m, and the ultraviolet source and the coil being mounted at an angle of 10°–90° to the horizontal;

an organic carbon stripper for stripping carbon dioxide gas from the oxidised sample; and a carbon dioxide detector for measuring the amount of carbon dioxide produced from the sample.

Said ultraviolet source and the coil are preferably mounted at an angle of about 35° to the horizontal.

The ultraviolet source preferably has a wavelength of about 254 nm and a power output of 10–100 watts, and more preferably 5–25 watts.

The ultraviolet source may be a low pressure mercury lamp, having a length of between about 20 cm and 92 cm and is typically about 46 cm long.

The quartz coil may have an overall uncoiled length of 3–10 m and is typically about 5,5 m long. The internal and external diameters of the quartz tubing may be 2–5 mm and 4–7 mm respectively and are typically about 3 mm and 5 mm respectively. The quartz coil may have between about 3 and 100 turns and preferably between about 20 and 80 turns. The coil typically has about 50 turns.

The internal diameter of the coil may be between about 10 and 35 mm and is preferably between about 25 and 30 mm.

The coil typically has an internal diameter of about 29 mm. The retention time of liquid in the coil may be between about 1 and 10 min., and preferably between about 3 and 7 min, sufficient to give complete conversion of metabolites in urine to $CO_2$. The retention time is typically about 3 min.

The apparatus may include an inorganic carbon stripper for removing, for example, inorganic carbon in the form of carbonate or bicarbonate ions from urine. Said inorganic carbon stripper, said organic carbon stripper, said carbon dioxide detector and said ultraviolet oxidation unit may be combined together in a single analytical instrument. Instead, the inorganic carbon stripper may be separate from said analytical instrument.

The inorganic stripper may comprise a tubular stripper unit defining a base, the unit including channelling means for channelling incoming bubbles of stripping gas, such as oxygen or nitrogen, into the base of the stripper unit so that the phase equilibrium of liquid in the stripper unit is disturbed near to the base of the stripper unit, thereby allowing improved gas/liquid separation so that higher concentrations of carbonate or bicarbonate may be removed from liquid in the stripper.

The invention will now be described, by way of example, with reference to the accompanying diagrammatic drawings in which.

BRIEF DESCRIPTION OF THE DRAWINGS

Figure 1:
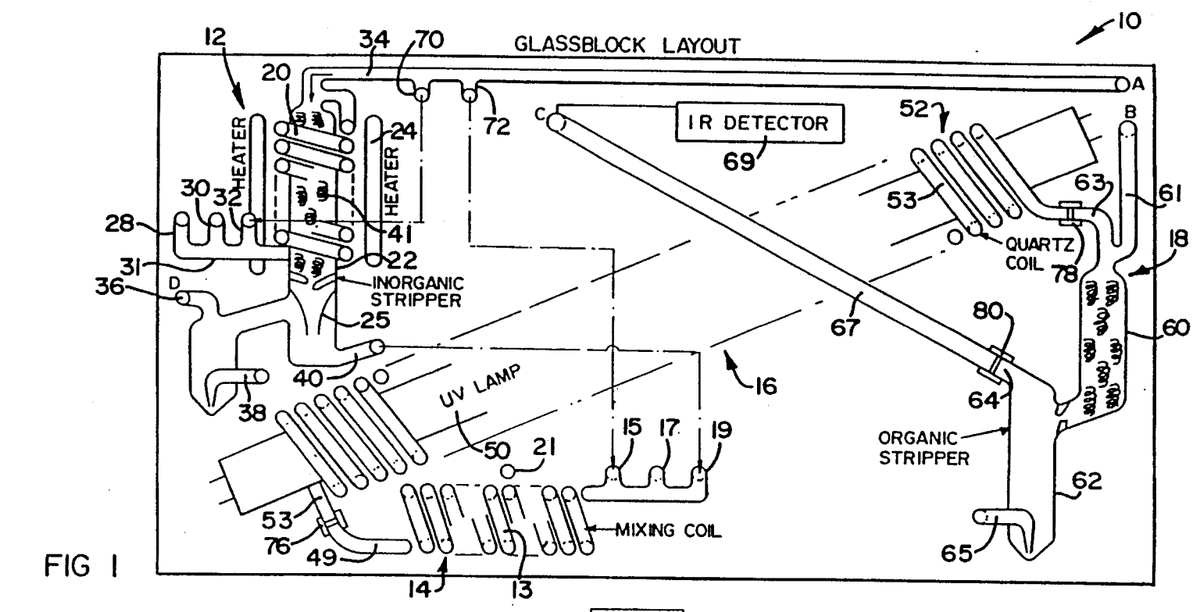
FIG. 1 is a schematic diagram of an apparatus, and a flow system therefor, for detecting abnormal levels of metabolites in the urine of a person who is suspected of suffering from a metabolic disorder, in accordance with the invention.
Figure 1A:
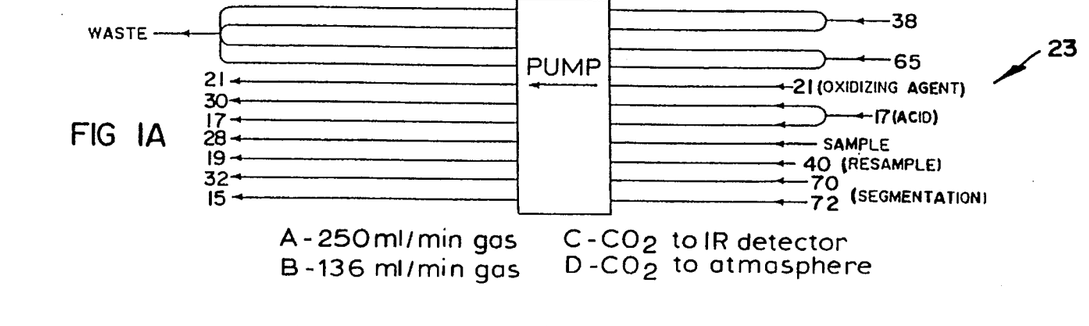
FIG. 1A is a schematic diagram of a peristaltic pump which controls the flow system shown in FIG. 1.

With reference to FIGS. 1 and 1A of the drawings, reference numeral 10 generally indicates an automatic apparatus, in the form of a single analytical instrument, for detecting abnormal levels of metabolites in the urine of a person who is suspected of suffering from a metabolic disorder, in accordance with the invention. The legend "ml/min gas" refers to carrier gas, segmentation gas and gas flow to the gas detector.

The apparatus 10 comprises a heated inorganic carbon stripper generally indicated by reference numeral 12, a mixing coil generally indicated by reference numeral 14, an ultra-violet oxidation unit generally indicated by reference numeral 16 and an organic carbon stripper generally indicated by reference numeral 18, enclosed in a sealed case. Liquid flow through the apparatus 10 is controlled by a peristaltic metering pump, generally indicated by reference numeral 23 in FIG. 1A, as described in South African Patent No. 90/6549, and available under the name "KelRon" (registered trade mark) in South Africa from Division of Water Technology, CSIR.

The inorganic carbon stripper 12 comprises an outer catalytic reaction coil 20 of glass tubing, a tubular stripper unit 22 and a heater jacket 24. Said tubing has an inner diameter of 3 mm. The coil 20 has an inner diameter of 17 mm and has 13 turns, and is filled with glass beads having an outside diameter of 2 mm.

In other embodiments of the invention, the inner diameter of said glass tubing can have other values ranging from 2 to 5 mm. Similarly, the inner diameter of the coil 20 can range from 15 to 20 mm, the number of turns can range from 10 to 20 and the outside diameter of the glass beads can range from 1,5 to 3,5 mm.

The stripper unit 22 has an outer diameter of 15 mm and a length of 80 mm, and is provided With an internal funnel-shaped channelling formation 25 for channelling incoming stripping gas towards the base of the unit 22, as described in further detail below.

In other embodiments of the invention, the outer diameter of the stripper unit 22 can have other values ranging from 14 to 19 mm. Similarly its length can have other values ranging from 60 to 100 mm.

The stripper 12 is provided with a sample inlet line 28, and acid inlet line 30 and a gas inlet line 32 for segmenting flow through the stripper 12. In this embodiment of the invention the gas is oxygen. However, in other embodiments of the invention the gas may be nitrogen, argon or helium, and is referred to hereafter for brevity simply as "the gas". The three inlet lines 28, 30, 32 feed into a common mixing line 31 which leads into the stripper 22 via the catalytic reaction coil 20. The ratio of mixing in the mixing line 31 is the product of the flow capacities of the lines 28, 30, 32.

The stripper 12 is, provided with a second gas inlet line 34 for feeding the gas into the stripper at a rate of 150 ml/min, a gas outlet line 36 for allowing the gas and carbon dioxide stripped from the solution inside the stripper to escape, a waste outlet line 38 and a re-sampling outlet line 40. The stripper 12 is packed with glass helicoils 41 having 6 turns and an outer diameter of 3 mm±1 mm, to increase its internal surface area.

In another embodiment of the invention (not shown), the stripper 12 is packed with glass beads having diameters of 1 to 5 mm or Raschig rings.

The heater jacket 24 maintains the stripper temperature during operation of the instrument at 60° C. In other embodiments of the invention, the temperature of the stripper can have other values between 40° and 85° C.

The mixing coil 14 comprises a coiled tube 13 having an internal diameter of 2 mm and has 13 turns. The coil 14 has an internal diameter of 18 mm.

In other embodiments of the invention, the number of turns of the coil can have other values ranging from 3 to 18 turns. Similarly, the inner diameter of the tube can range from 1 to 5 mm, and the internal diameter of the coil can range from 12 to 25 mm.

The mixing coil 14 is provided with a gas inlet line 15, a dilution inlet line 17, a sample inlet line 19 and an oxidizing agent inlet line 21 situated at the seventh turn of the coil 14.

The UV oxidation unit 16 comprises an elongate UV lamp 50 surrounded by a quartz glass coil 52. The lamp and coil are mounted at an angle of 35° C. with respect to the horizontal. The UV lamp is a low pressure 15 watt mercury lamp which emits radiation at a wavelength of 254 nm. The lamp 50 is 46 cm long. In other embodiments of the invention, the power of the UV lamp can have other values ranging between 5 and 1600 watts.

The coil 52 is of quartz tubing 53 having an internal diameter of 3 mm, an external diameter of 5 mm, and has 50 turns. The overall length (before coiling) of the quartz tubing 53 is 5,3 m. The coil has an internal diameter of 29 mm and retains liquid for 3 min.

In other embodiments of the invention, the internal and external diameters of the quartz tubing 53 can have other values ranging between 2 and 5 mm and 4 and 7 mm respectively. Similarly, the coil turns can range from 3 to 100 turns, the internal diameter can range from 10 to 35 mm, the overall length of the tube can range from 0,8 to 16 m and retain liquid for 1 to 10 min.

A feed line 49 connects the mixing coil 14 to the quartz coil 52 of the UV oxidation unit 16.

The organic carbon stripper 18 comprises a liquid/gas separation unit 60 and a liquid/waste unit 62 as a single piece. The stripper 18 is provided with a gas inlet line 61 and a sample inlet line 63 which together function as an atomizer nozzle. The sample inlet line 63 is connected to the quartz coil 52. The separation unit 60 has an internal diameter of 15 mm, a length of 80 mm and is packed with glass helicoils having an outside diameter of 3 mm and 6 turns to enlarge the total surface area in the stripper and facilitate $CO_2$ release from the solution.

In other embodiments of the invention, the inner diameter of the separation unit can have other values ranging from 14 to 19 mm, and the length can range from 60 to 100 mm.

The liquid/waste unit 62 has an internal diameter of 40 mm and a length of 40 mm. The liquid/waste unit 62 is provided with a gas exit tube 64 leading to a $CO_2$ infra-red detector (not shown) and a waste exit line 65. The exit tube 64 is 8 mm long and projects from the gas separator 62 at an angle of 35° C. to the horizontal. An extension tube 67 extends from the exit tube 64 to the detector. A moisture removal trap based on heat exchanging or a chemical compound such as a calcium chloride drying tube and a copper/zinc mesh trap (not shown) are provided between the extension tube 67 and the infrared detector to dry the gas entering the detector and to remove corrosive gases formed in the photochemical reactions respectively.

In other embodiments of the invention, the liquid/waste unit 62 has an internal diameter of 20 to 60 mm and the exit tube 64 has a length of 2 to 15 mm.

The apparatus 10 comprises a $CO_2$ infra-red detector 69 having a lower detection limit or sensitivity of 1.2 mmol/l of total urinary metabolites in liquid and is available as a "LEKTRON" detector from Lektratek. The concentration of total urinary metabolites is plotted and integrated as a single peak, employing creatinine as a concentration correction factor, by means of a computer utilising dedicated software. A "SPECTRA PHYSICS" desk integrator could be used instead or any desk top integrator.

A feed line 70 connects the gas inlet line 34 to the gas inlet line 32 and a feed line 72 connects the oxygen inlet line 34 to the oxygen inlet line 15. The sample inlet line 28 is connected to an autosampler available as a "KLINOLAB AUTO SAMPLER", supplied by Hook & Tucker, Croydon, England. The mixing coil 14 and the coil 52 are connected by a clip 76. The coil 52 and the inlet line 63 of the organic carbon stripper are connected by a clip 78. The exit tube 64 of the organic carbon stripper and the extension tube 67 are connected by a clip 80.

The layout of the peristaltic metering pump 23 is shown in FIG. 1A where the reference numerals used in FIG. 1 are used to indicate corresponding feed lines in FIG. 1A.

In use, the creatinine concentration in a urine sample is first determined according to the "SIGMADIAGNOSTICS" (registered trade mark) Creatinine Procedure No. 555 (1988) available from Sigma Diagnostics, USA for the analysis of creatinine in urine. Said Creatinine Procedure No. 555 (as re-issued in April 1989) is incorporated herein by reference. Any other valid creatinine concentration determination could also be used.

The sample is then diluted with deionised distilled water by a factor of 200 to adjust the concentration of metabolites in the sample to 50–1000 mmol metabolites/l, eg 600 metabolites/l. The sample is then fed via the autosampler at a rate of 6,3 ml min$^{-1}$ into the instrument 10 via the sample feed line 28. The sample is segmented by the introduction of gas through the gas feed line 32 at a rate of 0,8 ml min$^{-1}$ and is mixed with o-phosphoric or sulphuric acid via the inlet feed line 30 at a rate of 1 ml min$^{-1}$. Mixing takes place in the mixing line 31 as described above.

The solution containing the acid, sample and gas then passes through the catalytic reaction coil 20 where it is heated to 60° C. before entering the stripper 22. Inorganic carbon stripping takes place in the inorganic stripper 22 and the carbon dioxide produced leaves the inorganic stripper via the $CO_2$ output line 36. Gas for the inorganic stripping step is added in a controlled fashion via the gas inlet line 34. Gas flow is regulated by a flow- and pressure regulator (not shown). The gas assists in the volatilization of the $CO_2$ liberated in the stripper 12. The funnel-shaped formation 25 channels gas bubbles to the base of the stripper unit 22 as described above.

The sample is then re-sampled through the peristaltic pump and introduced into the mixing coil 14 via the inlet feed line 19 where the sample is cooled in the mixing coil. Additional acid is optionally fed in via the feed line 17, when required for dilution. The sample is then segmented by the introduction of gas via the feed line 15. It is then admixed with an oxidising agent namely potassium peroxodisulphate via the inlet feed line 21. The sample is then fed through the ultra-violet oxidizing unit 16 via the feed line 49 where metabolite organic compounds are oxidized to carbon dioxide by a photochemical oxidation process. Photonic cleavage, hydroxyl radicals and the ozone produced, enhance conversion of organic material to carbon dioxide.

Other gases produced in the oxidation process are not detected by the infrared detector which is highly selective for $CO_2$. The sample then passes through the organic stripper unit 18 where carbon dioxide is stripped from the sample and fed via the $CO_2$ outlet feed line 64 to the $CO_2$ infrared detector. The $CO_2$ level detected by the detector and related to the creatinine concentration of the sample is converted by the computer program into a transformed ratio (TR) value calculated as described above.

Figure 5:
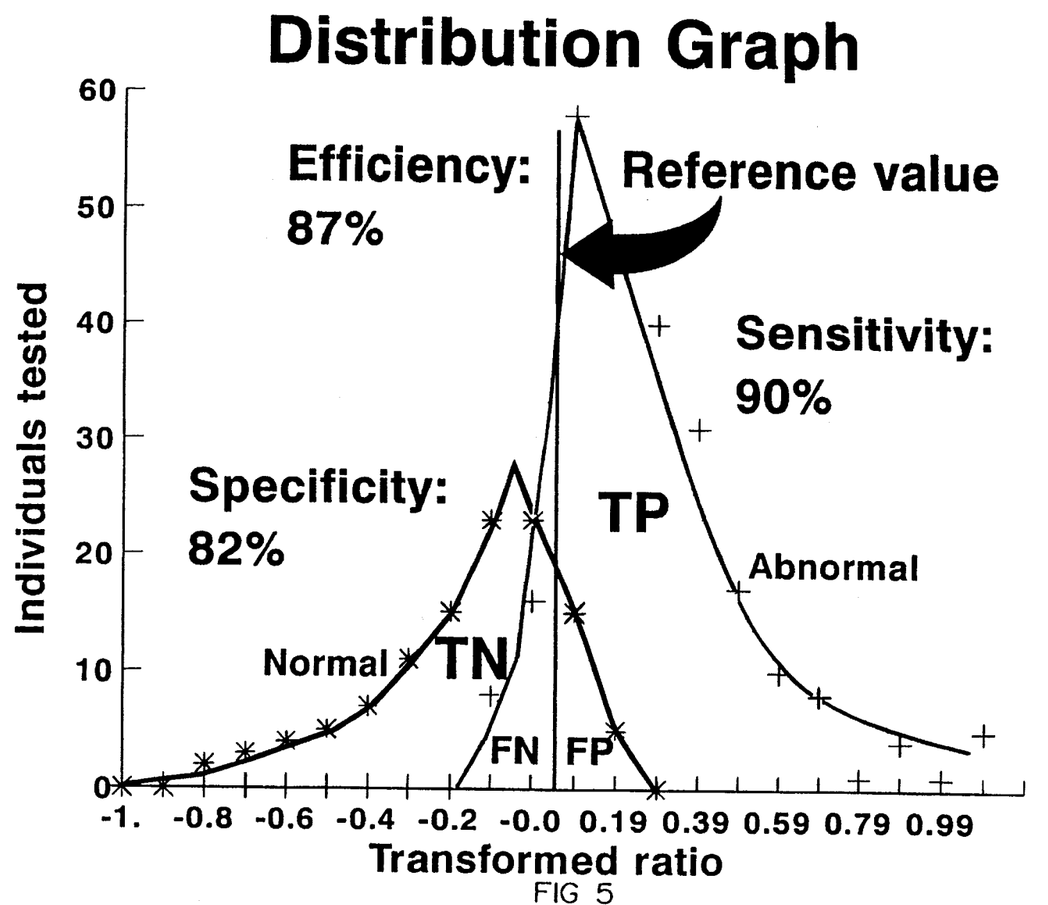
FIG. 5 is a general distribution graph showing the curves for the normal and abnormal cases with special reference to the true negative (TN), false negative (FN), false positive (FP) and true positive (TP) cases when a reference value (RV) of zero is selected.
Figure 6:
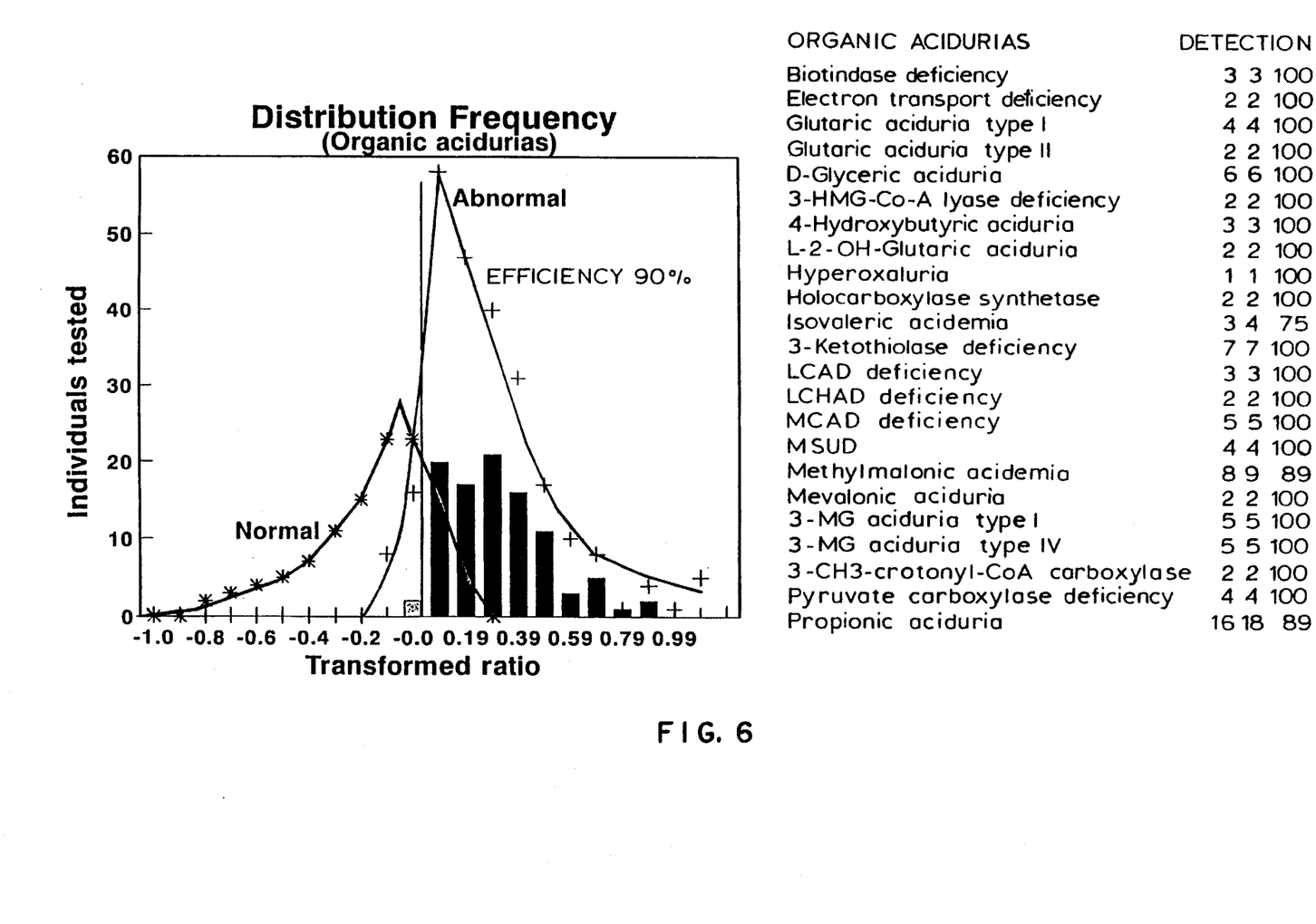
FIGS. 6 to 9 show the distribution frequency for organic acidurias, amino acidurias, purine and pyrimidine defects and carbohydrate and mucopolysaccharide defects respectively, with an indication of the efficiency of detection for each group of disorders; each Figure also contains, as an inset, a list of specific disorders with the number of cases tested, detected and expressed as a percentage.
Figure 7:
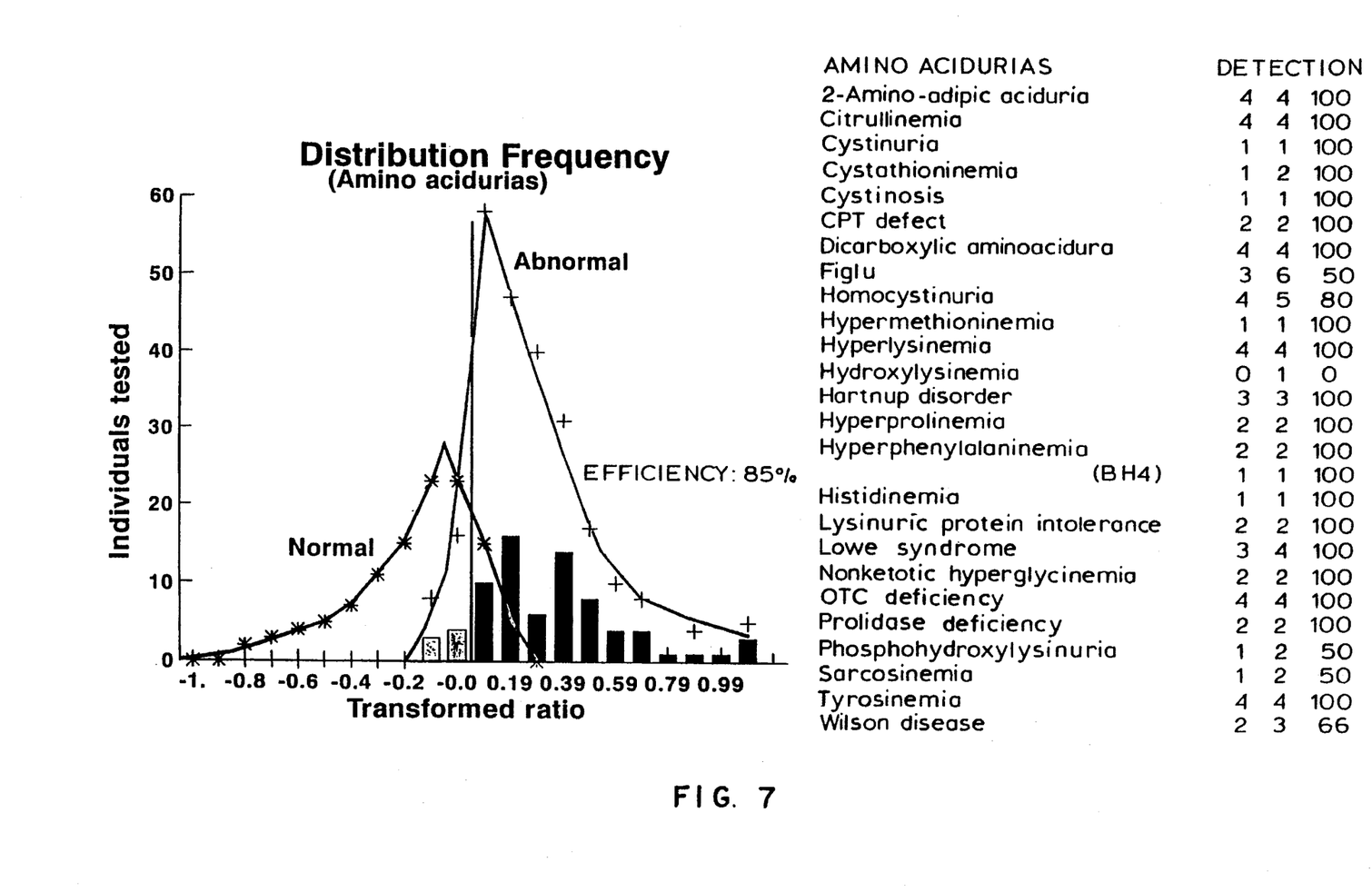
Figure 8:
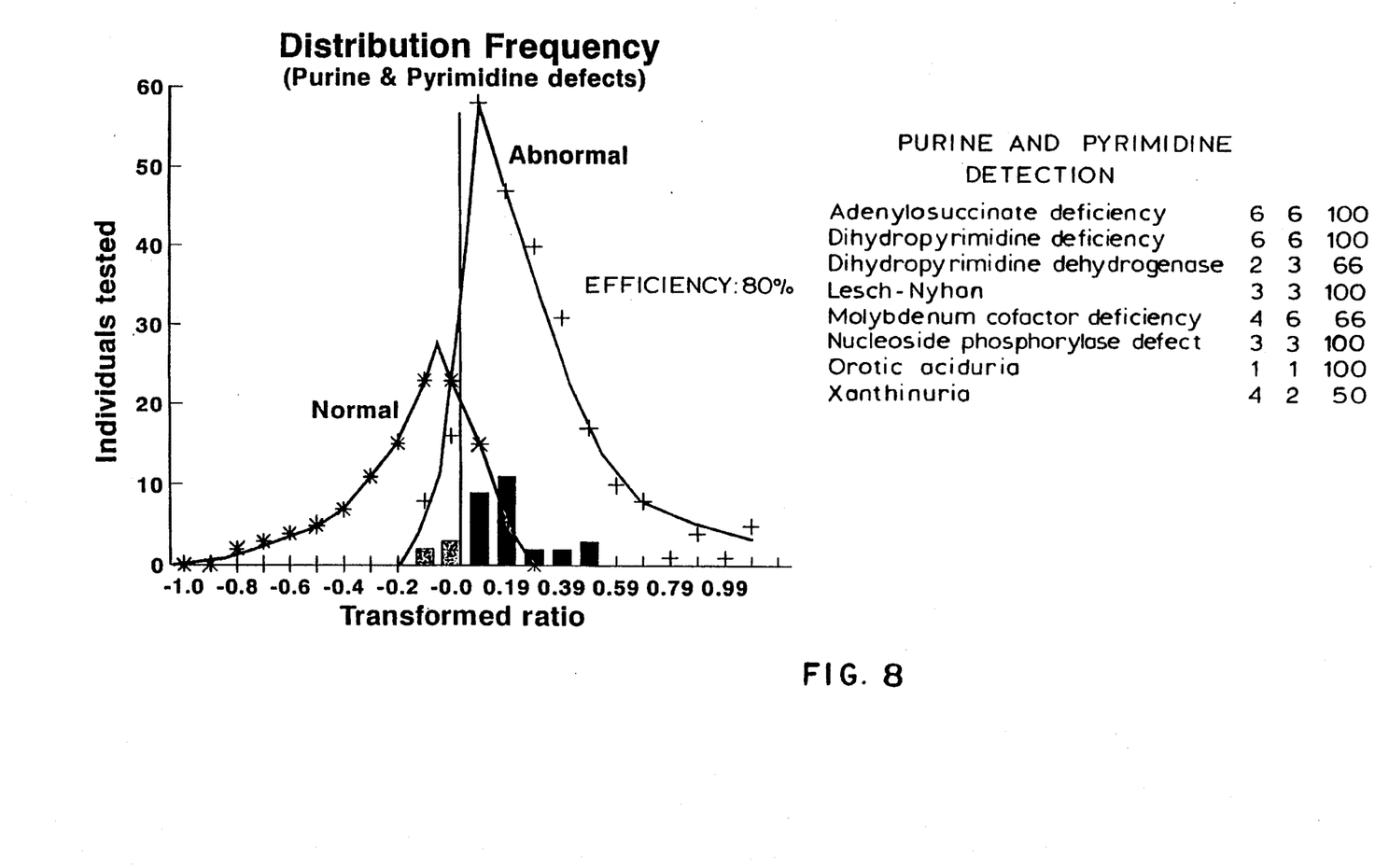
Figure 9:
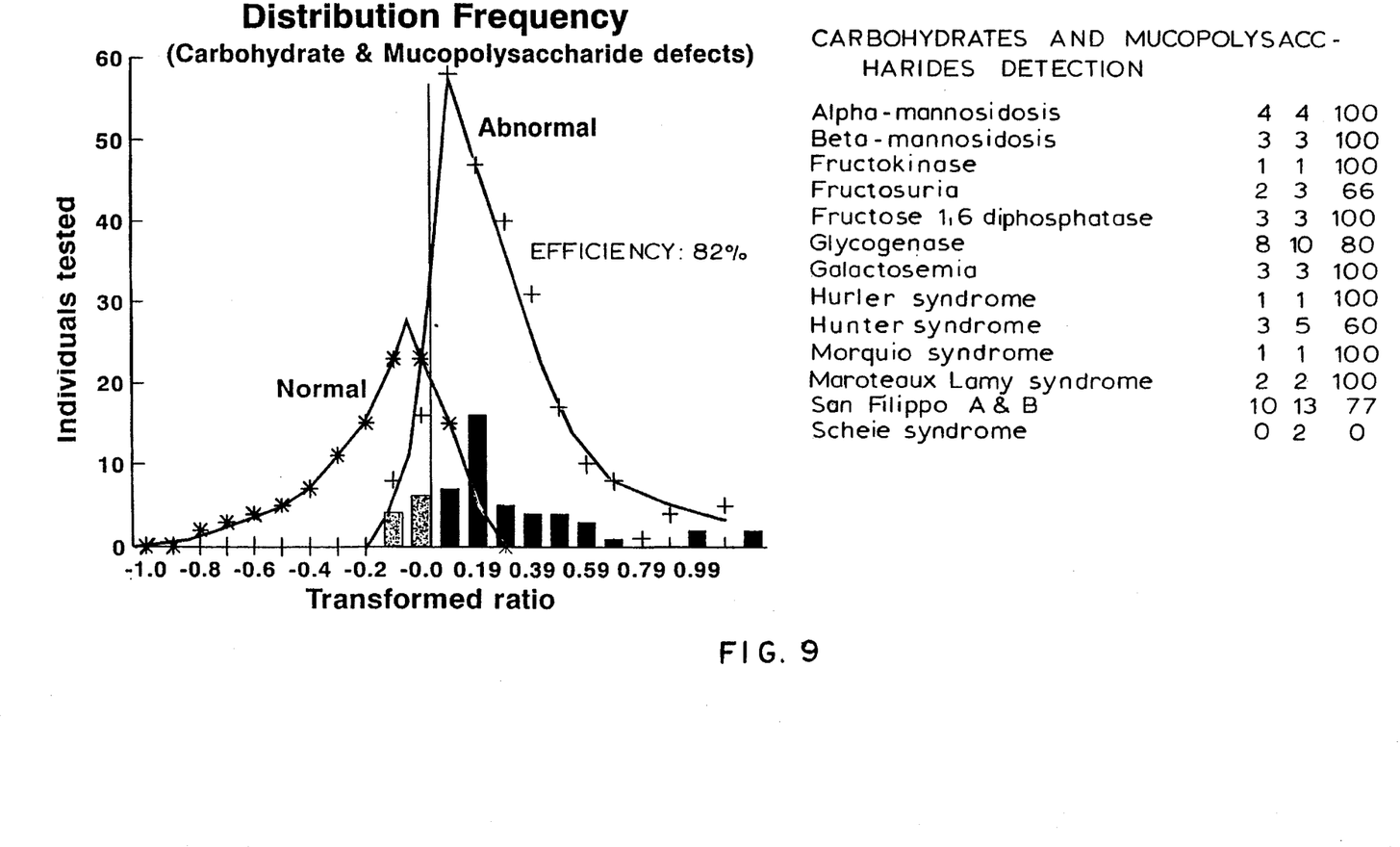

The results of analyses carried out on 125 "normal" persons as controls and 254 patients with a broad range of organic acidurias, amino acidurias, purine and pyrimidine defects and carbohydrate and mucopolysaccharide defects (these metabolic disorders had been detected previously by other means), are plotted in FIG. 5. At a 90% sensitivity rate and a 87% efficiency rate, the false positives were 18%.

Figure 10:
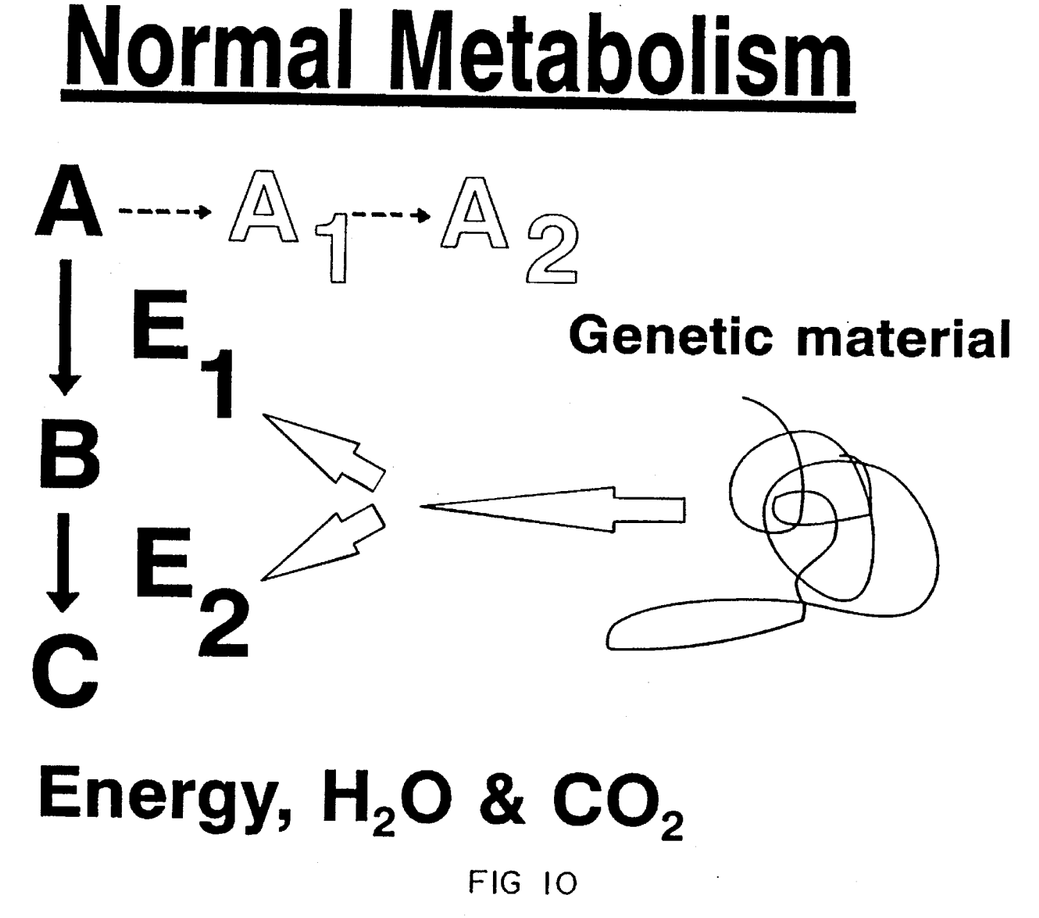
FIGS. 10 and 11 represent metabolic reaction schemes.

Without being bound by theory, the Applicants believe that, in broad terms, the metabolism of a normal person converts the substrates of metabolic pathways into energy, carbon dioxide and water as is shown schematically in FIG. 10 in which $E_1$ and $E_2$ represent normally functioning enzymes, and A, B and C represent the metabolites of a normal metabolic pathway. Generally, when a person suffers from a metabolic disorder, a malfunctional enzyme or the absence of an essential co-factor causes one or more intermediate(s) of the normal metabolic pathway or pathways to accumulate in the body. This deficiency is often inherited in an autosomal recessive way from both parents.

Figure 11:
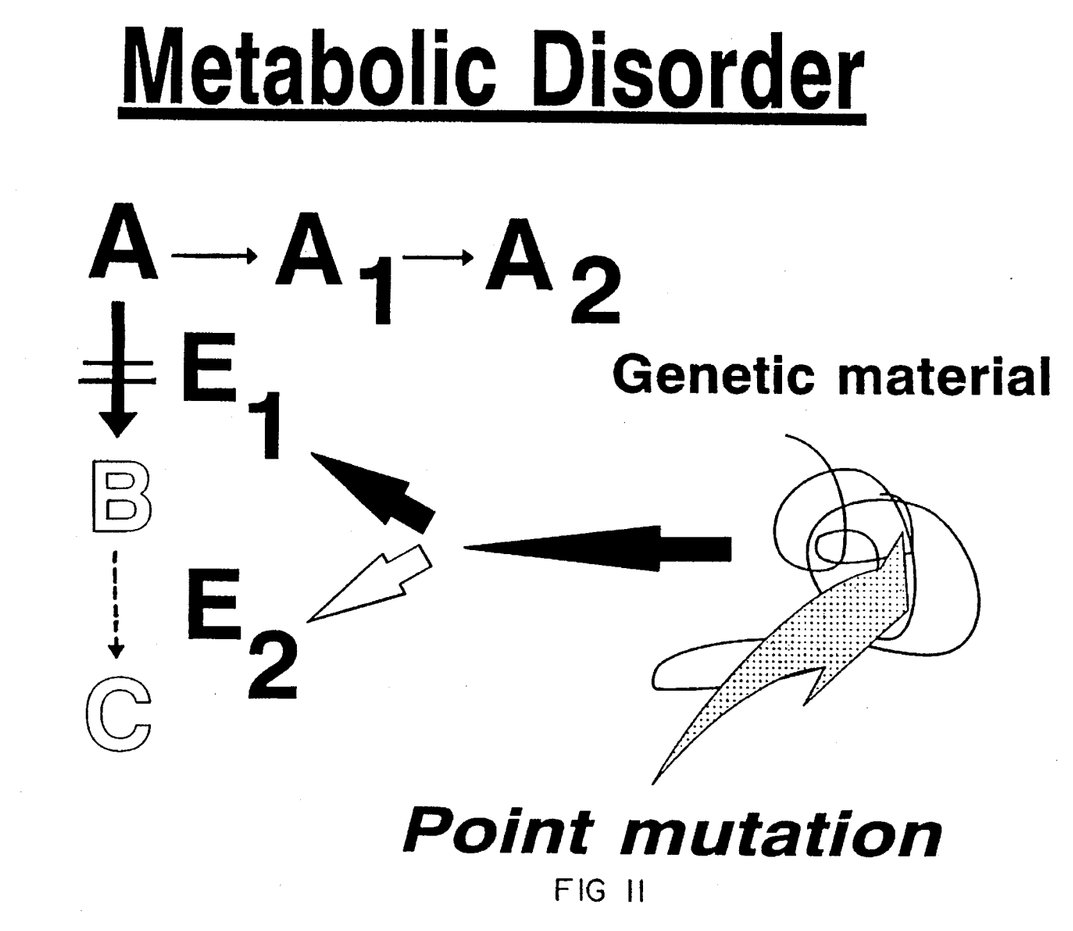

The accumulation of intermediates may trigger alternative metabolic pathways which produce metabolites which cannot be further metabolized by the body as is shown schematically in FIG. 11 in which $E_1$ represents a malfunctioning enzyme which triggers an alternative metabolic pathway $A1 \rightarrow A2$ which results in a build-up of abnormal metabolites in the body. The result of such a defect is that relatively large concentrations of such metabolites are excreted via the kidneys in the urine. Such a metabolic disorder may, therefore, be characterised by an abnormally high level of metabolites in the urine. This will, in turn, result in an increase in metabolites in the urine. Measurement of the metabolites in a urine sample will thus indicate an abnormally high level of metabolites in the sample and the likelihood of a metabolic disorder.

The concentration of urine samples obtained from different persons, however, varies due to factors such as metabolic rates and the intake of fluids. Consequently a concentration standard is necessary to enable urine samples from different persons to be compared. The Applicants have found that the use of creatinine as a concentration correction factor gives good results. The method is based on the finding that the amount of creatinine excreted via the urine on a daily basis remains generally constant and although it may vary to a degree from person to person depending on factors such as sex, age and the total fat-free muscle mass of the person, it is relatively little affected by factors such as physical activity, urine volume or diet. The creatinine content of a urine sample can thus be used as an internal standard against which the level of metabolites in the urine can be measured.

As described above, the concentration of total urinary metabolites in a urine sample is expressed as a so-called "transformed ratio" (TR) with values ranging normally from −1 to +1 calculated as described above. As described, if the operator of the instrument 10 chooses a reference value (RV) of zero, then any sample displaying a TR value between 0 and +1 is considered abnormal and any sample displaying a TR value between 0 and −1 is considered normal. Thus, patients whose urine displays a TR value between 0 and +1 should be subjected to further metabolic tests.

With reference to FIG. 5, a reference value of zero on the transformed ratio (TR) scale gave a sensitivity (SENS) of 90% and a specificity (SPEC) of 82%. This would ultimately result in an efficiency (expressed as a percentage of all results that are true results) of 87%. As described above, the reference value (RV) may be adjusted to provide either better sensitivity (SENS) or specificity (SPEC).

With further reference to FIG. 5, the results show that 13% of the patients in whom metabolic disorders had been diagnosed, present a negative transformed ratio (TR) value and 18% of normal patients showed a positive transformed ratio (TR) value, i.e. the method showed 13% "false negative" values and 18% "false positive" values. The Applicants believe, however, that said 13% may, in part, be ascribed to the fact that some of these patients were already receiving treatment which could have reduced the concentration of metabolites in the urine.

The Applicants believe it is an advantage of the invention that the normal procedures used for the identification of metabolic disorders such as organic acid analysis by gas chromatography and mass spectrometry, or amino acid analysis using an amino acid analyzer, which are both time-consuming and expensive, are circumvented. It is thus possible to screen a large number of urine samples and to select only those samples which fall above a certain cut-off value for further analysis. The method of the invention thus acts as a valuable screening procedure which, in turn, may serve to reduce the large number of samples which currently have routinely to be subjected to sophisticated metabolic tests at a considerable cost in time, labour and money. The Applicants believe that the method will serve as an inexpensive and fast way of obtaining a reliable new risk indicator for the detection of especially amino acidurias, glycosurias, hyperpurine-pyrimidine urias and organic acidurias.

The Applicants have also found that said length of the quartz tubing and said power output of the ultra-violet source cause complete oxidation of essentially all metabolites in a sample so that the instrument gives accurate results. The Applicants have found, in particular, that the apparatus and method of the invention allow the recovery and determination of essentially all of the metabolites present in urine. Tests conducted on urine samples containing known amounts of amino acidurias, glycosurias, hyperpurine-pyrimidine urias and organic acidurias showed that essentially all of the metabolites present were recovered and detected. The Applicant has, further, found that locating the quartz coil at an angle of 35° to the horizontal, reduces the amount of diffusion which takes place in the liquid which passes through the coil. This serves to keep the sample being analyzed contained in a fairly small volume of liquid as it passes through the apparatus. This, in turn, results in improved peak separation so that a greater number of samples may be analyzed in a given time.

We claim:

1. A method for the preliminary screening for the presence of abnormal levels of metabolites in the urine of a human or animal suspected of suffering from a metabolic disorder, the method comprising the steps of:

(a) determining the amount of creatinine in mmol/l in the urine of the human or animal, the amount of creatinine serving as an internal standard useful in correcting for variation in urine concentration;

(b) measuring the total urinary metabolites content in the urine by oxidizing the total urinary metabolites to carbon dioxide and measuring the amount of carbon dioxide produced;

(c) calculating a transformed ratio, the transformed ratio (TR) corresponding to the total urinary metabolites content corrected for urine concentration using the internal standard;

(d) comparing the transformed ratio calculated in (b) with a reference value, the reference value representing the transformed ratio of the total urinary metabolites content of urine from humans or animals who do not suffer from a metabolic disorder; and wherein an increase in the transformed ratio above the reference value is abnormal and suggestive of a metabolic disorder.

2. A method as claimed in claim 1, in which measuring the concentration of total urinary metabolites content is effected in the range 50–1000 mmol metabolites/l.

3. The method claim 1 in which total urinary metabolites are oxidized to carbon dioxide by means of ultra-violet irradiation.

4. A method as claimed in claim 1, which includes the step of removing inorganic material from the urine, prior to measuring the concentration of total urinary metabolites content in the urine.

5. The method of claim 1 wherein the transformed ratio of step (c) is calculated using the following formula:

TR=A−B where

A=log total urinary metabolite content

B=log (urinary creatinine content+1)×C+D where C is a constant, and D is a constant.

6. The method of claim 5 wherein C=0.906.

7. The method of claim 5 wherein D=1.96.

* * * * *